United States Patent [19]

Lypchuk

[11] Patent Number: 5,526,811

[45] Date of Patent: Jun. 18, 1996

[54] APPARATUS AND PROCESS FOR DETERMINING THE SOURCES OF BIOMAGNETIC ACTIVITY

[75] Inventor: Tanya Lypchuk, San Diego, Calif.

[73] Assignee: Biomagnetic Technologies, Inc., San Diego, Calif.

[21] Appl. No.: 78,451

[22] Filed: Jun. 15, 1993

[51] Int. Cl.$^6$ .................................................. A61B 5/05
[52] U.S. Cl. .................................. 128/653.100; 324/244; 324/248
[58] Field of Search .................... 128/653.1; 324/244, 324/248, 260, 262

[56] References Cited

U.S. PATENT DOCUMENTS

| | | | |
|---|---|---|---|
| 4,977,896 | 12/1990 | Robinson et al. | 128/653.1 |
| 5,136,242 | 8/1992 | Abraham-Fuchs | 128/653.1 X |
| 5,170,119 | 12/1992 | Sekihara et al. | 128/653.1 X |
| 5,228,443 | 7/1993 | Tatar | 128/653.1 X |

*Primary Examiner*—Ruth S. Smith
*Attorney, Agent, or Firm*—Gregory Garmong

[57] ABSTRACT

An apparatus and process for making biomagnetic measurements of a biological organism permits the internal sources of the activity to be identified. An array of dipole sources is identified by providing a plurality of biomagnetic sensors disposed at locations external to the biological organism, measuring a measured biomagnetic response at each of the sensors, and amplifying and filtering the measured biomagnetic response. A solution of dipole sources within the biological organism is determined by forward calculating a computed biomagnetic response at each of the sensors resulting from the biomagnetic activity of a plurality of dipole sources, each of which dipole sources contributes a normalized total signal strength at the sensors, and solving for the strengths of each of the dipole sources by a minimum norm estimation procedure. Convergence on the solution is aided by iteratively removing from the determination those apparent sources that contribute only a small portion of the signal strength, and then resolving the resulting relationship.

18 Claims, 4 Drawing Sheets

Z=10

Z=8

Z=6

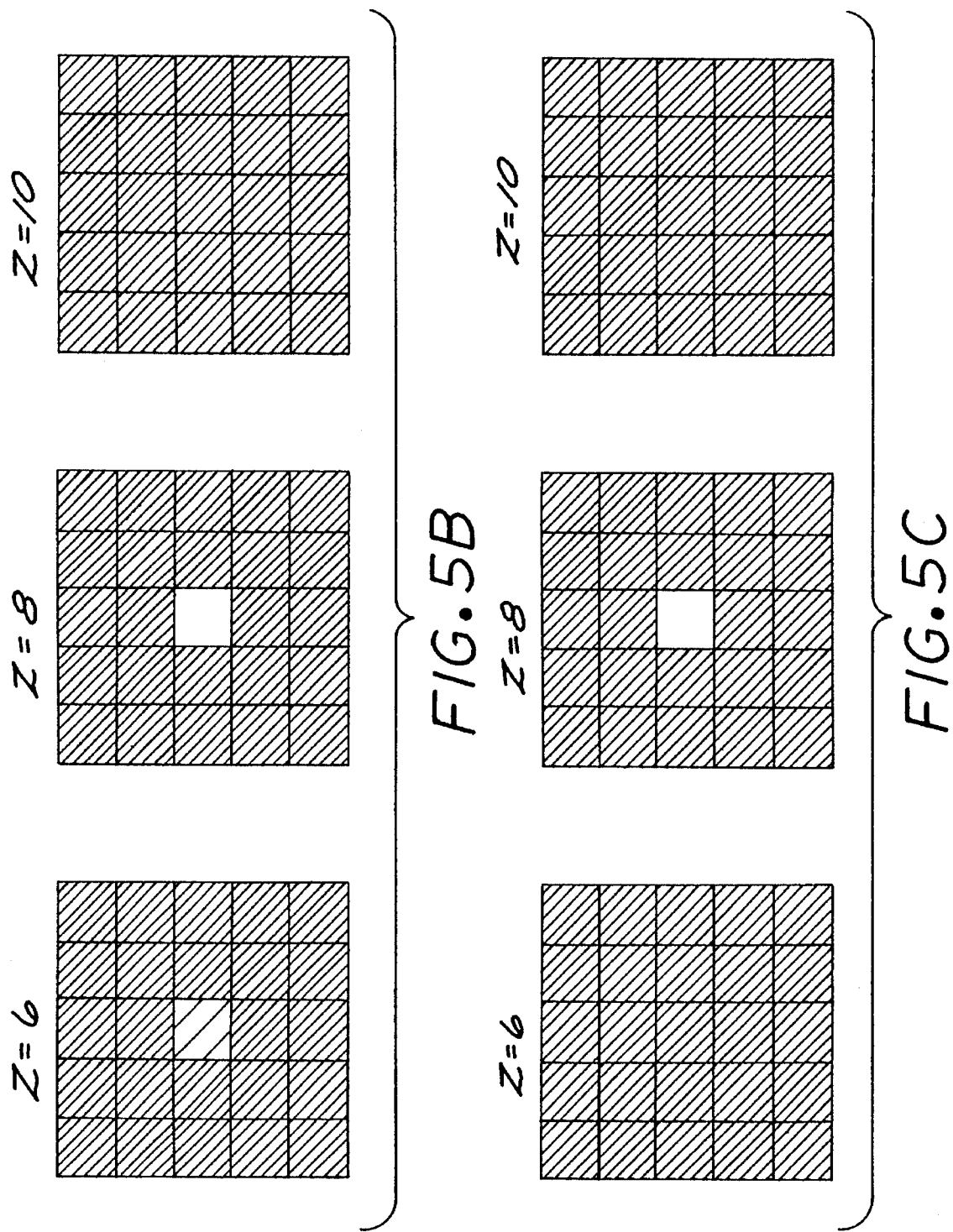

APPARATUS AND PROCESS FOR DETERMINING THE SOURCES OF BIOMAGNETIC ACTIVITY

BACKGROUND OF THE INVENTION

This invention relates to measuring magnetic fields produced by living organisms, and, more particularly, to determining the sources of such biomagnetic activity from external measurements.

Living organisms produce magnetic fields that can be measured noninvasively with sensors positioned outside of the organism. These magnetic fields arise from electrical activity within the organism. Measurement of the magnetic fields can lead to an understanding of the electrical activity. For example, the measurement of magnetic fields produced by the brain can lead to an understanding of the mechanisms of perception and sensory response, as well as to the normal functioning of the brain and conditions that lead to illnesses and abnormalities.

Biomagnetometers are devices that measure the small magnetic fields produced by a living organism. The biomagnetometer typically includes a number of sensors arranged in an array external to the organism, which measure the magnetic field at a number of locations. Each sensor typically has a magnetic field pickup coil that may be a magnetometer or a gradiometer. When a small magnetic flux change penetrates the pickup coil, a small electrical current flows in the coil. This small current is detected by a sensitive detector of electrical currents, preferably a Superconducting Quantum Interference Device, known by the acronym "SQUID". The output of the various SQUIDs, after amplifying, filtering, and signal conditioning, is provided to a computer which stores and analyzes the data. The SQUIDs operate only at superconducting temperatures, and to attain the best system performance the pickup coils and SQUIDs are usually placed into a cryogenically cooled dewar. Because the biomagnetic fields produced by the body are so small compared to the magnetic fields of the earth and many types of electrical apparatus, it is common to place the subject of the biomagnetic study into a magnetically shielded room that excludes external magnetic and radio frequency fields.

The course of development of biomagnetometers has led to ever-increasing numbers of sensors (pickup coils and SQUIDs) in each unit. As of this writing, biomagnetometers with 37 sensors are available commercially, and even larger numbers of sensors are likely in future units. One impetus to increasing the number of sensors is that the larger amount of information available from the array of sensors offers the promise of magnetically imaging the source region during operation of the magnetic fields. That is, with a sufficient amount of information it becomes possible to form pictures or maps of activity in organs such as the human brain and heart.

The fundamental problem in analyzing sources of magnetic activity in the brain within the context of operation of a biomagnetometer is that the number of potential sources is greater than the number of sensors. Exact solutions are therefore not possible. Additionally, the magnetic field produced within the organism passes through several media (e.g., tissue, bone, air) before being measured, thereby complicating the analysis. In order to produce optimal solutions within these constraints, various analytical techniques to solving this "inverse problem of biomagnetism" have been utilized.

One common analytical approach has been to assume that the externally measured magnetic field is produced by a single dipole source or some small number of dipole sources, and to calculate the location, orientation, and strength of the source(s) from the external measurements. This approach is questionable because of its oversimplification of the physiology of the organism, but has been useful in a number of contexts. More rigorous approaches involve mathematical analyses of the data gathered by the sensors, such as the lead field synthesis technique described in U.S. Pat. No. 4,977,896. The minimum norm estimation technique also shows promise, because it provides a solution optimized according to physical principles. However, it may not yield fully acceptable results in some circumstances.

There is therefore a need for an improved biomagnetometer and approach to making biomagnetic measurements wherein the magnetic field sources within the subject organism are imaged based upon the external measurements of magnetic field. The present invention fulfills this need, and further provides related advantages.

SUMMARY OF THE INVENTION

The present invention provides an apparatus and process for making external, noninvasive biomagnetic measurements of a biological organism, and relating those measurements to the internal magnetic field sources of the subject that produce the measured results. The technique can utilize the numbers of sensors on available apparatus, and can also be adapted for use with even larger arrays of sensors as they become available. The approach of the invention is particularly useful where the biomagnetic sources lie at varying depths within the body.

In accordance with the invention, a process for making biomagnetic measurements of a biological organism comprises the steps of providing a plurality of biomagnetic sensors disposed at locations external to the biological organism, measuring a measured biomagnetic response signal at each of the sensors, and amplifying and filtering the measured biomagnetic response signals. In array of dipole sources within the biological organism that produces the externally measured biomagnetic response is determined by forward calculating a computed biomagnetic response at each of the sensors resulting from the biomagnetic activity of a plurality of dipole sources, each of which dipole sources contributes a normalized total signal strength at the sensors, and solving for the biomagnetic signal strengths of each of the dipole sources by a minimum norm estimation procedure using the computed biomagnetic response and the amplified and filtered biomagnetic response signal.

Further in accordance with the invention, an apparatus for making biomagnetic measurements of a biological organism comprises a plurality of biomagnetic sensors, means for measuring a measured biomagnetic response of a biological organism by each of the sensors, and means for amplifying and filtering the measured biomagnetic response. There is, additionally, means for determining an array of dipole sources within the biological organism by forward calculating a computed biomagnetic response at each of the sensors resulting from the biomagnetic activity of a plurality of dipole sources, each of which dipole sources contributes a normalized total signal strength at the sensors, and solving for the strengths of each of the dipole sources by a minimum norm estimation procedure utilizing the computed biomagnetic response and the amplified and filtered measured biomagnetic response.

In the preferred implementation, the forward calculation is performed by choosing and fixing an array of candidate dipole sources within the biological organism as the linear relationship $$[A_{ij}][y_j]=[b_i].$$

In this relationship, $y_j$ is the contribution of the jth dipole source to the total biomagnetic signal; $b_i$ is the measured biomagnetic response of the ith sensor; $A_{ij}=f_i(r_j,q_j)$, $f_i$ is the effect on the ith sensor of the jth dipole source; $r_j$ is the source position of the jth dipole source; and $q_j$ is the dipole moment of the jth dipole source. A key feature is that $$\|\bar{f}(r_j,q_j)\|=1$$

for all of the dipole sources. Here, $$\bar{f}(r_j,q_j) \triangleq [f_1(r_j,q_j),\ldots,f_n(r_j,q_j)]$$

where n is the number of sensors. This solution, $y_j$, indicates the relative contributions of the biomagnetic signals of the dipole sources.

These relationships are utilized to obtain the minimum norm solution for the $y_j$ values. Once these values are known the dipole strengths are determined through the relation $$\bar{f}(r_j,y_j*q_j)=y_j\,\bar{f}(r_j,q_j)$$

Here, as above $$\|\bar{f}(r_j,q_j)\|=1$$

The strength of the jth dipole is obtained by multiplication as $$y_j*\|q_j\|.$$

When this process is implemented, it is often found that many of the dipole sources appear to make minimal contribution to the measured magnetic field. Such dipole sources producing low signal strength are likely either physically present but related to noise or processes not of interest, or are artifacts of the process. To improve the precision of the analysis so that attention may be focused on the dipole sources of physiological interest as related to particular processes within the subject, an iterative approach may be followed. In a second round of the determination process, those dipoles which contribute less than a preselected amount to the signal strength are removed from the determination, while the other dipoles determined in the substep of solving are retained. Then the substep of solving for the signal strengths of the remaining dipole sources by a minimum norm estimation procedure is repeated, on the smaller universe of dipole sources under evaluation. After several rounds of calculation, it is usually observed that the determination converges to a set of dipole sources. Simulations under controlled conditions have demonstrated that this final set of dipole sources resulting from the process closely approximates the actual set of dipole sources that produce the externally measured magnetic fields. It is particularly significant that the approach does not favor near-surface sources over deep sources.

The present approach is an important advance in the art of biomagnetometers, and of making biomagnetic measurements and imaging the biomagnetic sources within a subject. In many instances, the biomagnetometer has limited usefulness when the readouts of the sensors are provided as raw data. The analysis of the present approach, when used in conjunction with the biomagnetometer sensors and their information, permits the biomagnetometer to "image" magnetic sources in the body. Other features and advantages of the invention will be apparent from the following more detailed description of the preferred embodiments, taken in conjunction with the accompanying drawings, which illustrate, by way of example, the principles of the invention.

BRIEF DESCRIPTION OF THE DRAWINGS

FIG. 5(B) is after a second iteration; and FIG. 5(C) is after a third iteration.

DETAILED DESCRIPTION OF THE INVENTION

Figure 1:
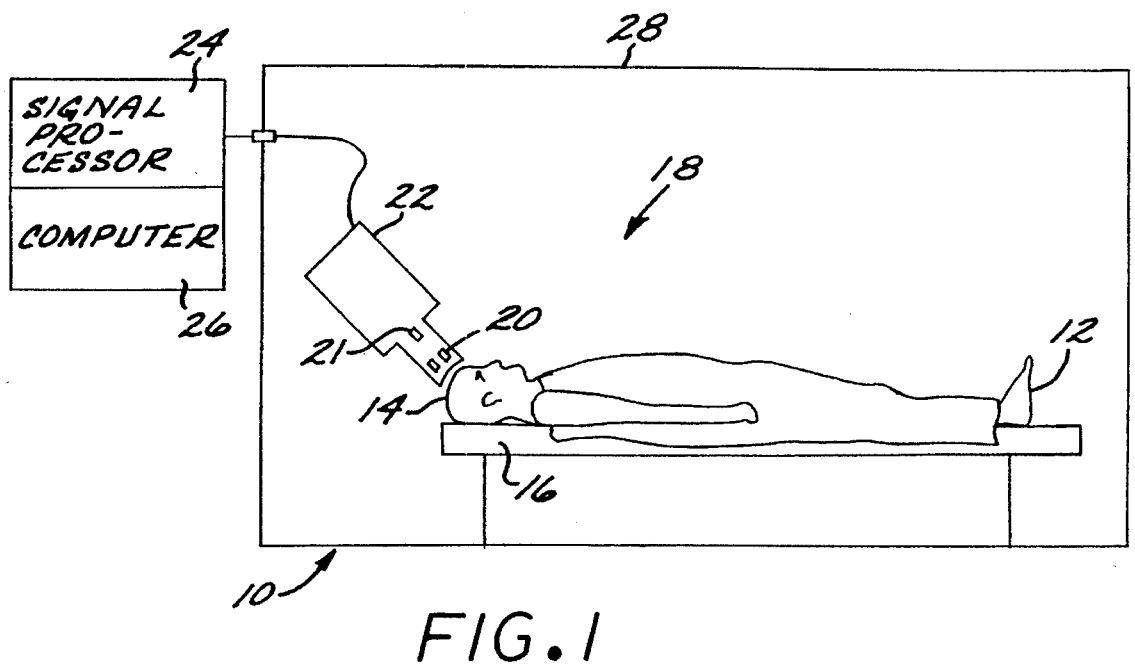
FIG. 1 is a diagrammatic depiction of a biomagnetometer.
Figure 6:
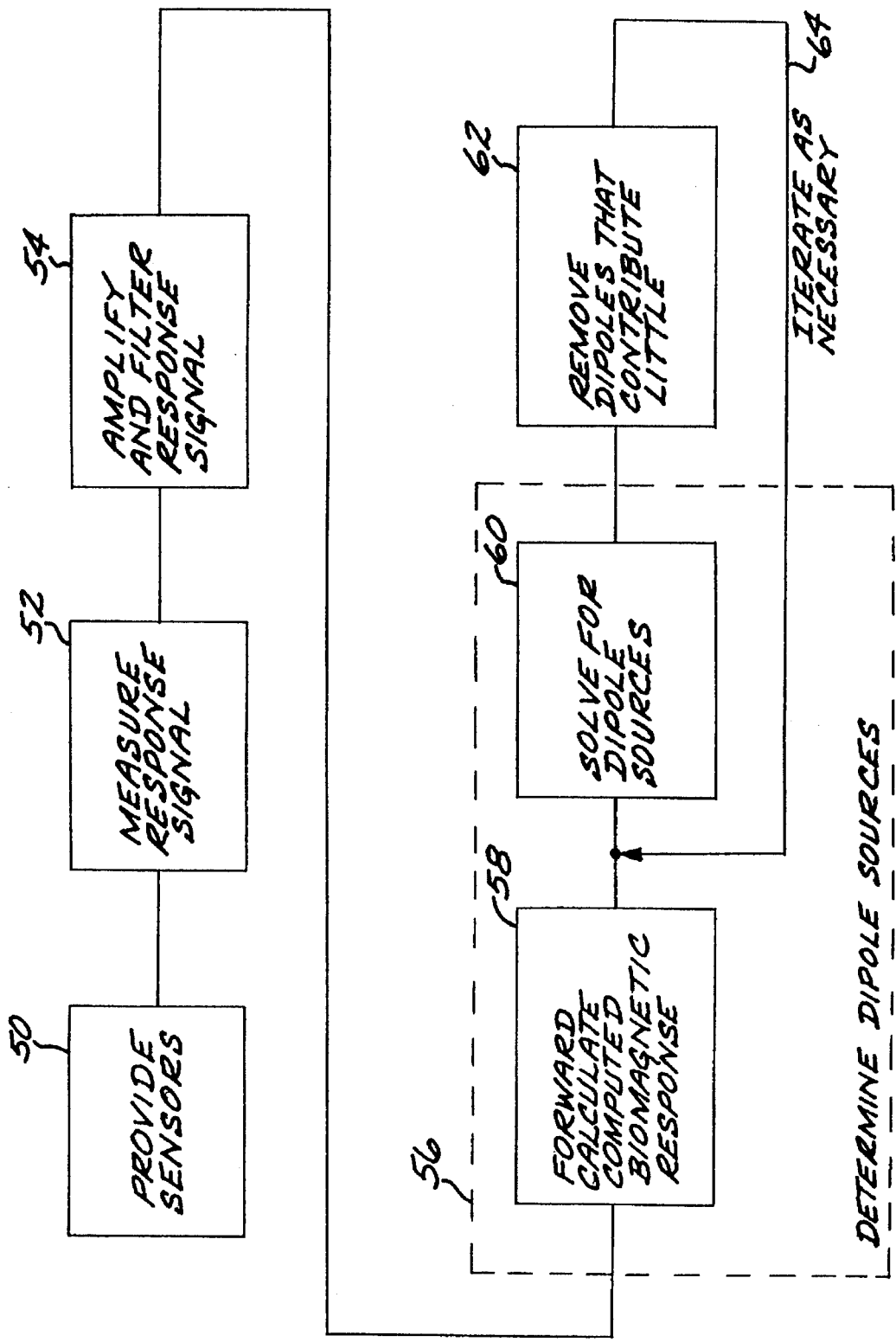
FIG. 6 is a process flow chart for an embodiment of the invention.

An apparatus for practicing the present invention is illustrated in FIG. 1, and a process that may be practiced in accordance with the invention is illustrated in FIG. 6. Referring to FIG. 1, the present invention is preferably embodied in an apparatus 10 for obtaining biomagnetic data from the body 12 of a human patient or subject. More specifically, the data is often obtained from biomagnetic sources within the head 14 of the person, from the heart, or from some other portion of the body. The person reclines upon a table 16 (or sits on a chair) in proximity to a biomagnetometer 18. The biomagnetometer 18 includes a plurality of magnetic field pickup coils 20 for measuring small magnetic fields. The pickup coils may be magnetometers or gradiometers, or of other configuration as may be appropriate for a particular application.

In each operating sensor channel, the output signal of the magnetic field pickup coil 20 is detected by a detector, preferably a superconducting quantum interference device 21 (SQUID). The pickup coil 20 and its associated SQUID detector 21 are collectively termed a "sensor", see numeral 50 in FIG. 6. Both the magnetic field pickup coil 20 and the SQUID 21 are maintained at a cryogenic operating temperature within a dewar 22. In the preferred practice a large number of pickup coils 20 and SQUIDs 21 are located in one dewar 22, or multiple dewars may be used.

Figure 2:
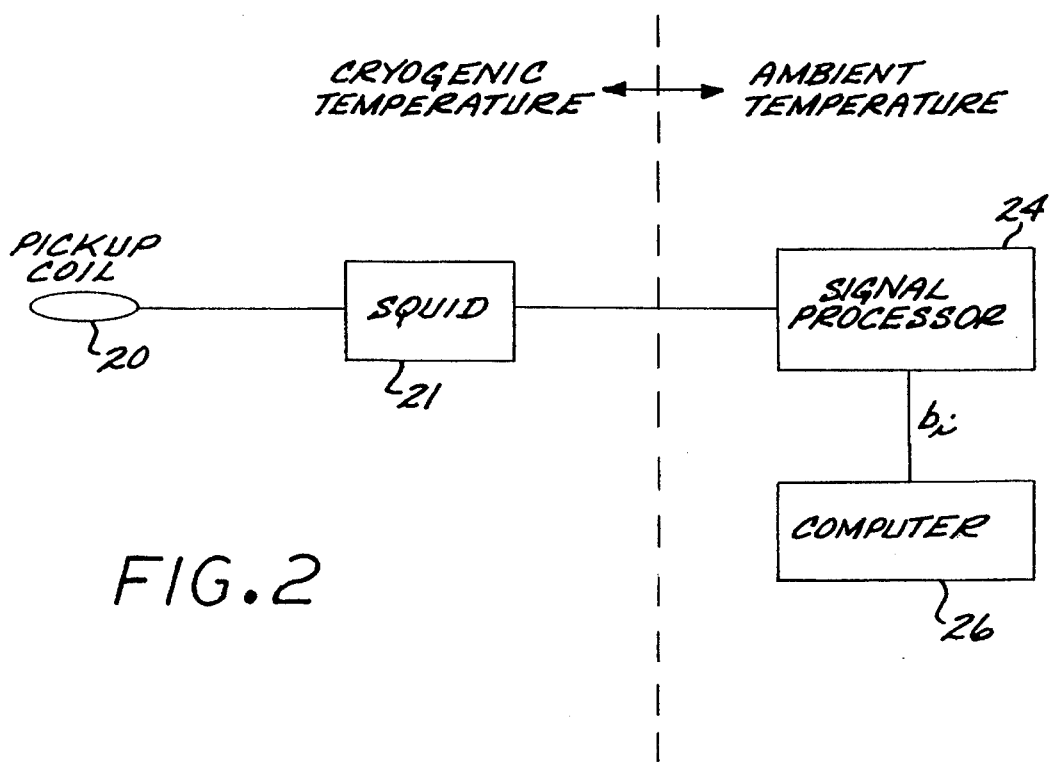
FIG. 2 is a block diagram of a single sensor channel.

The electronics arrangement of the biomagnetometer 18 is illustrated structurally in FIG. 1 and functionally for a single complete sensor channel in FIG. 2. The magnetic signals from the brain are picked up by the magnetic field pickup coil 20 in the dewar 22, which produces a small electrical current output signal when penetrated by a magnetic flux. The output signal of the pickup coil 20 is detected by a detector, in this case the SQUID 21. The SQUID 21 thus detects the magnetic field flux and produces a measured biomagnetic response signal as an electrical current, numeral 52 of FIG. 6. After acquisition, The output signal of the SQUID is processed in an ambient-temperature signal processor 24, which includes balancing, gain, amplifying, and filtering circuitry, numeral 54 of FIG. 6, and stored as a signal $b_i$ (the ith sensor channel) in a computer 26 as a function of time. Each sensor channel results in a record of its response to the magnetic field produced by all of the sources within the subject brain 14, as those sources act simultaneously on the pickup coil of the sensor channel.

The pickup coil 20 and the body 12 of the patient are preferably, but not necessarily, enclosed within an enclosure 28 (also termed a magnetically shielded room or MSR) that shields the apparatus and magnetic field source from external influences. By screening off the external influences, the amount of signal processing and filtering required to obtain a meaningful indication of the biomagnetic field is reduced.

These portions of the biomagnetometer are available commercially, and their basic structure and operation are known. The operation of SQUIDs and ambient-temperature SQUID electronics are disclosed in U.S. Pat. Nos. 3,980,076; 4,079,730; 4,386,361; and 4,403,189. A biomagnetometer is disclosed in U.S. Pat. No. 4,793,355. Magnetically shielded rooms are disclosed in U.S. Pat. Nos. 3,557,777 and 5,043,529. The disclosures of all of these patents are incorporated herein by reference.

Figure 3:
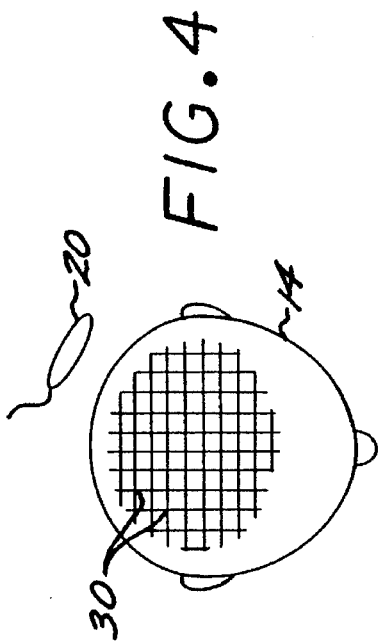
FIG. 3 is a schematic representation of the effect of a dipole source on an external sensor.

An array of dipole sources is determined within the biological organism, numeral 56 of FIG. 6. FIG. 3 illustrates the relationships used in determining the effect of a single dipole source on the measured bioelectromagnetic response of a single pickup coil. A dipole source (r,q) of fixed location and moment is positioned at a location 30 within the brain 14. The dipole source (r,q) produces a field f(r,q) on the pickup coil 20, which is located at a position r with respect to the dipole source at sampling location 30. The effect of the single dipole source (r,q) on the single pickup coil 20 is b=f(r,q)+noise errors (if any). In this relation, r is the source position, q is the source dipole moment, and b is the output signal of the pickup coil 20. Where there are numerous dipole sources $(r_j,q_j)$ acting on a single pickup coil 20, the signal from the pickup coil 20 is written as $$b = \sum_{j=1}^{m} f(r_j, q_j),$$

where m is the number of dipole sources. In addition, this relation is linear with respect to the dipole moments $q_j$. In particular, the jth dipole moment is scaled in strength by an amount $y_j$. The signal due to that dipole is scaled by the same amount $y_j$. This relation can be written $$f(r_j, y_j * q_j) = y_j f(r_j, q_j).$$

More generally, for i pickup coils, the relations may be written as $$b_i = \sum_{j=1}^{m} y_j f_i(r_j, q_j).$$

For simplified writing as a matrix equation, $f_i(r_j,q_j)$ is written as $A_{ij}$, $b_i$ is written as vector b, and $y_j$ is written as vector y, resulting in the matrix relation $$b = Ay.$$

In performing a forward solution, numeral 58 of FIG. 6, the candidate dipole source is of a known position r and orientation q. In the prior approach of Crowley et al. set forth in "Minimum Norm Estimation of Current Distributions in Realistic Geometries", Proc. VII International Congress on Biomagnetism (Plenum Press), 1989, the dipole sources were taken to be of unit strength in the generation of the matrix A. A minimum norm estimation was applied to determine the dipole array of minimum strength required to produce the observed external measurements. Under this definition of the matrix A, the minimum norm estimation results in minimization of the vector y, which is the strength of the dipole array. As a result, shallow sources near to the surface of the brain (i.e., minimum magnitude of the y values) are strongly favored in the solution and there may be a lack of coincidence between the actual dipole source array and that determined from this approach.

In the present approach, $A_{ij}=f_i(r_j,q_j)$, where $(r_j,q_j)$ is a dipole of fixed location $r_j$ and fixed orientation $q_j$. However, the dipole moment $q_j$ is chosen such that $$\|\bar{f}(r_j,q_j)\|=1$$

for all of the dipole sources. Here, $$\bar{f}(r_j,q_j) \triangleq [f_1(r_j,q_j), \ldots, f_n(r_j,q_j)]$$

where n is the number of sensors. That is, each column of the matrix $A_{ij}$, which corresponds to a single dipole source, is normalized so that the sum squared of the values in each column is the same for all columns. The columns of the matrix $A_{ij}$ are therefore of unit norm, and the jth column represents the shape of the magnetic signal due to the jth dipole.

With this adjustment to the matrix $A_{ij}$, the minimum norm solution is determined, numeral 60 of FIG. 6, using well known techniques by minimizing Ay−b using the matrix manipulation $y=(A^TA)^{-1}A^Tb$. The resulting minimum norm solution is not biased toward either shallow or deep sources, since the components of y represent signal strengths, not dipole strengths as in the approach of Crowley et al.

Figure 4:
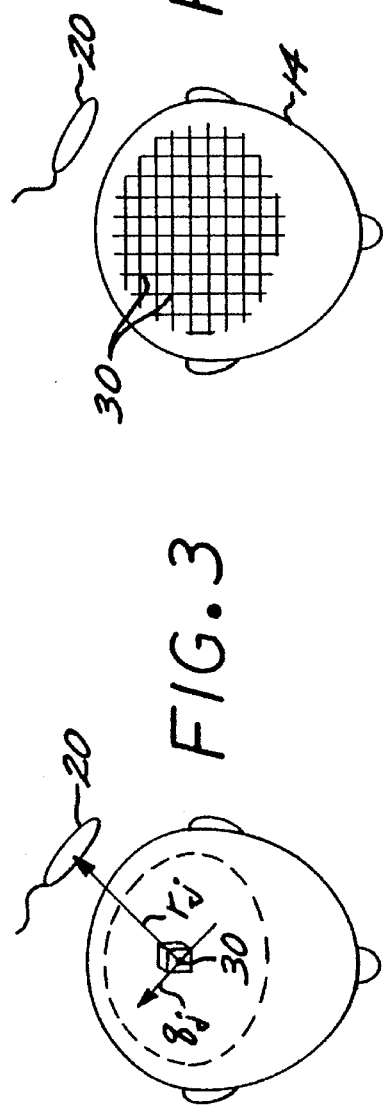
FIG. 4 is a schematic representation of an array of dipole sources within the head of a human subject.

This portion of the process may be implemented using a small number of sampling locations 30 that are known to have physiological significance. Alternatively, as illustrated in FIG. 4, there may be selected a large number of sampling locations that essentially fill the space of the brain or other portion of interest of the subject under study.

When the process just described is performed, particularly in the latter case where a large number of sampling locations are evaluated, some of the dipole sources are, not unexpectedly, determined to have small signal strengths. These dipoles with weak signals may be due to physiological activity that is not of interest to a particular study or unrelated to a particular stimulus, to physiologically based noise, or to artifacts of the calculation. These dipole sources producing a weak signal strength can be eliminated in order to "sharpen" the imaging of the stronger dipole sources, by utilizing additional optional processing.

To eliminate weak sources from consideration, the determination of the dipole sources is iteratively repeated with the weak sources removed from the matrix $A_{ij}$, reducing j by one for each weak source that is eliminated, numeral 62 of FIG. 6. The $b_i$ values remain the same, as they are measured sensor responses. In practice, all dipole sources of a signal strength less than some preselected value are eliminated. For example, if a source has a determined signal strength of less than 10 percent of the strength of the strongest dipole, it may be concluded to be of insufficient strength to warrant further interest and be eliminated. Then the matrix equation b=Ay is solved under these new conditions. If there are a substantial number of dipole sources remaining with strengths less than the preselected number, those sources may be eliminated from the A matrix and the matrix equation again solved. It is observed that after 3–4 iterations, numeral 64 of FIG. 6, the determination typically converges toward a correct solution, as verified by simulations using known dipole sources.

Figure 5A:
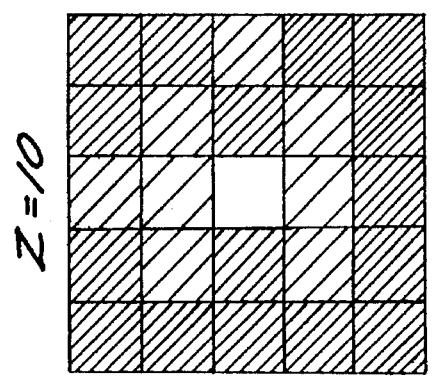
FIG. 5(A) is a schematic display of the results of a simulation of the present approach, after a first iteration.
Figure 5A:
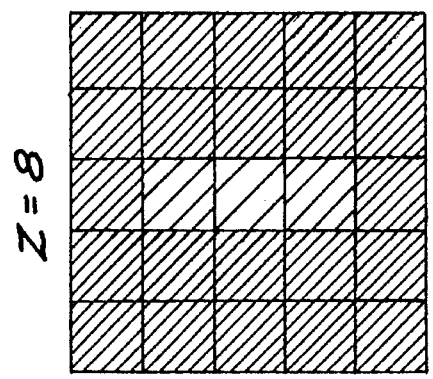
Figure 5A:
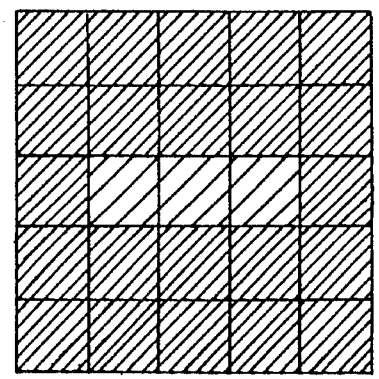

In order to verify the operability of the approach, a simulation was performed using a known source and the approach of the invention. A dipole source having a dipole moment of (10,0,0) nano amp meters was placed at a location of (0,0,8) centimeters within a sphere of radius 12 centimeters. An array of 37 pickup coils was placed about the sphere, external to the sphere and with the center coil of the array at (0,0,12) centimeters. A cubic grid was established with points ranging from x=−4 to x=+4, y=−4 to y=+4, and z=6 to z=10, for a total of 75 grid locations arranged as a cube. The source cutoff was 40 percent, so that weaker sources were eliminated in succeeding iterations. FIG. 5(A) depicts the source signal strength determined for a first iteration, in the planes at z=6, z=8, and z=10. (In FIGS. 5(A)–(C), the denser the shading, the smaller the signal.) FIG. 5(B) depicts the source signal strength determined for a second iteration at the same locations, and FIG. 5 (C) depicts the source signal strength determined for a third iteration at the same locations. The first iteration shows a divergence of the determined location of the source, the second iteration shows some convergence, and the third iteration shows that the determined location has converged to the correct location of (0,0,8).

The present process thus identifies the correct location of the dipole after three iterations. By contrast, a conventional minimum norm estimation, performed without iterations, tends to misidentify the location of the dipole as being closer to the surface (i.e., at to z=10 rather than z=8) than its actual location.

The present approach provides an apparatus and process for determining the location and strength of magnetic field sources within living subjects, without bias toward shallow sources. Although particular embodiments of the invention have been described in detail for purposes of illustration, various modifications may be made without departing from the spirit and scope of the invention. Accordingly, the invention is not to be limited except as by the appended claims.

What is claimed is:

1. A process for making biomagnetic measurements of a biological organism, comprising the steps of:

providing a plurality of biomagnetic sensors disposed at locations external to the biological organism;

measuring a measured biomagnetic response signal at each of the sensors;

amplifying and filtering the measured biomagnetic response signal;

determining an array of dipole sources within the biological organism by forward calculating a computed biomagnetic response at each of the sensors resulting from the biomagnetic activity of a plurality of dipole sources, each of which dipole sources contributes a normalized total signal strength at the sensors, and solving for the strengths of each of the dipole sources by a minimum norm estimation procedure using the computed biomagnetic response and the amplified and filtered biomagnetic response signal.

2. The process of claim 1, including the additional substeps of the step of determining, after the substep of solving, of removing those dipoles from the determination which contribute less than a preselected amount to the signal strength while retaining the other dipoles determined in the substep of solving, and repeating the step of solving for the strengths of the remaining dipole sources by a minimum norm estimation procedure.

3. The process of claim 1, including the additional step, after the step of determining, of displaying the location of the dipole sources.

4. The process of claim 1, wherein the step of providing includes the step of placing the sensors adjacent to a brain of the biological organism.

5. The process of claim 1, wherein the step of providing includes the step of placing the sensors adjacent to a heart of the biological organism.

6. The process of claim 1, including the additional step, after the step of amplifying and filtering, and before the step of determining, of:

storing the values of the amplified and filtered signal in a memory.

7. The process of claim 6, including the additional step, after the step of storing and before the step of determining, of:

recalling the values of the amplified and filtered signal from the memory.

8. The process of claim 1, including the additional step, before the step of measuring, of:

providing a biological organism having biomagnetic sources located at varying depths below a surface of the biological organism.

9. A process for making biomagnetic measurements of a biological organism, comprising the steps of:

providing a plurality of biomagnetic sensors disposed at locations external to the biological organism;

measuring a measured biomagnetic response at each of the sensors;

amplifying and filtering the measured biomagnetic response signal;

determining an array of dipole sources within the biological organism as the linear relationship $[A_{ij}][y_j]=[b_i]$, where $y_j$ is the signal strength of the jth dipole source, $b_i$ is the amplified and filtered biomagnetic response signal of the ith sensor, $A_{ij}=f_i(r_j,q_j)$, $f_i$ is the effect on the ith sensor of the jth dipole source $(r_j,q_j)$ having fixed location and dipole moment, and $(r_j,q_j)$ is chosen such that $\|f(r_j,q_j)\|=1$ for all of the dipole sources, and solving for the dipole strengths of the dipole sources.

10. The process of claim 9, including the additional substeps of the step of determining, after the substep of solving, of removing those dipoles from the determination which contribute less than a preselected amount to the signal strength while retaining the other dipoles determined in the substep of solving, and repeating the step of solving for the strengths of the remaining dipole sources by a minimum norm estimation procedure.

11. The process of claim 9, including the additional step, after the step of determining, of displaying the location and relative strengths of the dipole sources.

12. The process of claim 9, wherein the step of providing includes the step of placing the sensors adjacent to a brain of the biological organism.

13. The process of claim 9, wherein the step of providing includes the step of placing the sensors adjacent to a heart of the biological organism.

14. The process of claim 9, including the additional step, after the step of amplifying and filtering, and before the step of determining, of:

storing the values of the amplified and filtered signal in a memory.

15. The process of claim 14, including the additional step, after the step of storing and before the step of determining, of:

recalling the values of the amplified and filtered signal from the memory.

16. The process of claim 9, including the additional step, before the step of measuring, of:

providing a biological organism having biomagnetic sources located at varying depths below a surface of the biological organism.

17. Apparatus for making biomagnetic measurements of a biological organism, comprising:

a plurality of biomagnetic sensors;

means for measuring a measured biomagnetic response of a biological organism by each of the sensors;

means for amplifying and filtering the measured biomagnetic response;

means for determining an array of dipole sources within the biological organism by forward calculating a computed biomagnetic response at each of the sensors resulting from the biomagnetic activity of a plurality of dipole sources, each of which dipole sources contributes a normalized total signal strength at the sensors, and solving for the strengths of each of the dipole sources by a minimum norm estimation procedure utilizing the computed biomagnetic response and the amplified and filtered measured biomagnetic response.

18. The apparatus of claim 17, further including:

means for storing the amplified and filtered measured biomagnetic responses.

\* \* \* \* \*